US008604220B2

(12) United States Patent
Jullian et al.

(10) Patent No.: US 8,604,220 B2
(45) Date of Patent: Dec. 10, 2013

(54) ISOLATION OF SIMALIKALACTONE E AND USE THEREOF AS A MEDICAMENT, IN THE TREATMENT OF MALARIA

(75) Inventors: Valérie Jullian, Toulouse (FR); Alexis Valentin, Toulouse (FR); Eric Deharo, Tarnos (FR); Geneviève Bourdy, Ramonville Saint Agne (FR); Franciane Ho-A-Kwie, Aix-en-Provence (FR); Nadia Cachet, Saint Jean de Vaulx (FR)

(73) Assignee: Institut de Recherche Pour le Development, Marseille Cedex (FR)

( * ) Notice: Subject to any disclaimer, the term of this patent is extended or adjusted under 35 U.S.C. 154(b) by 124 days.

(21) Appl. No.: 13/378,888

(22) PCT Filed: Jun. 17, 2010

(86) PCT No.: PCT/FR2010/000447
§ 371 (c)(1),
(2), (4) Date: Feb. 29, 2012

(87) PCT Pub. No.: WO2010/146257
PCT Pub. Date: Dec. 23, 2010

(65) Prior Publication Data
US 2012/0149767 A1    Jun. 14, 2012

(30) Foreign Application Priority Data

Jun. 18, 2009  (FR) ..................................... 09 02959

(51) Int. Cl.
*C07D 311/00* (2006.01)
(52) U.S. Cl.
USPC ......................................................... 549/275
(58) Field of Classification Search
USPC ......................................................... 549/275
See application file for complete search history.

(56) References Cited

PUBLICATIONS

Cachet et al. Antimicrobial Agents and Chemotherapy (2009), 53(10), 4393-4398.*
International Search Report from International Application No. PCT/FR2010/000447.
Bertani, S., et al.; Simalikalactone D is Responsible for the Antimalarial Properties of an Amazonian Traditional Remedy made with Quassia Amara L. (Simaroubaceae); Journal of Ethno-Pharmacology 108 (2006); pp. 155-157.
Vigneron M. et al.; Journal of Ethnopharmacology, 2005, 98 (3), pp. 351-360.
Bertani S. et al; Journal of Ethnopharmacology, 2005, 98(1-2), pp. 45-54.
Z. Guo et al.; Current Medicinal Chemistry, 2005, 2, pp. 173-190.
Guido F et al.; International Journal for Parasitology, 1998, 28, pp. 635-640.

Curcino Vieira I. and Braz-Filho R; Studies in Natural Products, Elsevier, 2006, 33, pp. 433-492.
W. Trager and J.B. Jensen, Science, 1976, 193 (4254): p. 673-675.
Lambros, C. and J.P. Vanderberg; The Journal of Parasitology, 1979, 65(3): p. 418-420.
Ribaut, C. et al., Malaria Journal, 2008, 7(1): p. 45.
Desjardins R.E. et al.; Antimicrob. Agents Chemother, 1979, 16: pp. 710-718.
F. Benoit et al.; Trans. Roy. Soc. Trop. Med. Hyg. 89: pp. 217-218.
Ifediba, T. and J.P. Vanderberg; Nature, 1981, 294 (5839): p. 364-366.
Sall, C. et al.; Bioorganic & Medicinal Chemistry Letters, 208, 18(16): p. 4666-4669.
Bertani, S. et al., *Evaluation of French Guiana Traditional Antimalarial Remedies*, Journal of Ethnopharmacology 98 (2005) 45-54.
Bertani, S. et al., *Simalikalactone D is Responsible for the Antimalarial Properties of an Amazonian Traditional Remedy Made With Quassia Amara L. (Simaroubaceae)*, Journal of Ethnopharmacology 108 (2006) 155-157.
Curcino Vieira, I. J. et al., *Quassinoids: Structural Diversity, Biological Activity and Synthetic Studies*, Rahman (Ed.) Studies in Natural Products Chemistry, vol. 33, Elsevier B.V. (2006) 433-492.
Francois, G. et al., *Antimalarial and Cytotoxic Potential of Four Quassinoids from Hannoa Chlorantha and Hannoa Klaineana, and Their Structure-Activity Relationships*, International Journal for Parasitology 28 (1998) 635-640.
Guo, Z. et al., *Biological Active Quassinoids and Their Chemistry: Potential Leads for Drug Design*, Current Medicinal Chemistry, 12 (2005) 173-190.
Benoit, F. et al., *Antimalarial Activity in vitro of Cochlospermum Tinctorium Tubercle Extracts*, Transaction on the Royal Society of Tropical Medicine and Hygiene, 89 (1995) 217-218.
Desjardins, R. E. et al., *Quantitative Assessment of Antimalarial Activity in vitro by a Semiautomated Microdilution Technique*, Antimicrobial Agents and Chemotherapy, vol. 16, No. 6 (1979) 710-718.
Ifediba, T. et al., *Complete in vitro Maturation of Plasmodium Falciparum Gametocytes*, Nature, 294 (1981) 364-366, [online] [retrieved Jun. 6, 2012]. Retrieved from the Internet: <URL: http://www.nature.com/nature/journal/v294/n5839/pdf/294364a0.pdf>. 2 pages.
Lambros, C. et al., *Synchronization of Plasmodium Falciparum Erythrocytic Stages in Culture*, J. Parasitol. 65(3) (1979) 418-420.
Ribaut, C. et al., *Concentration and Purification by Magnetic Separation of the Erythrocytic Stages of All Human Plasmodium Species*, Malaria Journal (2008) [online] [retrieved Jun. 6, 2012]. Retrieved from the Internet: <URL: http://www.malariajournal.com/content/7/1/45/>. 3 pages.
Sall, C. et al., *Design, Synthesis, and Biological Activities of Conformationally Restricted Analogs of Primaquine With a 1,10-phenanthroline Framework*, Bioorganic & Medicinal Chemistry Letters 18 (2008) 4666-4669.
Trager, W. et al., *Human Malaria Parasites in Continuous Culture*, Science, 193 (1976) 673-675.
Vigneron, M. et al., *Antimalarial Remedies in French Guiana: a Knowledge Attitudes and Practices Study*, Journal of Ethnopharmacology 98 (2005) 351-360.

\* cited by examiner

*Primary Examiner* — Nizal Chandrakumar
(74) *Attorney, Agent, or Firm* — Alston & Bird LLP (57) ABSTRACT

The subject of the invention is a novel molecule, Simalikalactone E, which can be extracted from the plant *Quassia amara*, and also the use thereof as a medicament, in particular in the prevention and treatment of malaria.

9 Claims, 6 Drawing Sheets

Table 1: Antiplasmodial activity and cytotoxicity of SkE

| | P.falciparum strains | | | | Cell lines | | |
|---|---|---|---|---|---|---|---|
| | F32 | FcB1 | W2 | W2 Indochina | Vero | MCF7 | THP1 |
| | Tanzania | Colombia | Indochina | Gametocytes | | | |
| | | | Asexual | | | | |
| SkE [a1] | 68 ± 12 [b] | 45 ± 32 | 24 ± 10 | 1.12 ± 0.4 μM | 6574 ± 264 | 47 ± 2 | 33 ± 5 |
| SkD [a2] | NT [c] | 1 | NT | NT | 58 ± 11 | < 20 [d] | < 2 [d] |
| CQ [a3] | 36 ± 3 | 167 ± 32 | 196 ± 16 | NT | > 500 [e] | > 500 [e] | > 500 [e] |
| MFQ [a4] | 401 | 16 | 108 | NT | NT | >10³ | >10³ |
| PMQ (μM) [a5] | 6.17 ± 1.2 | 8.9 ± 1.1 | 7.14 ± 0.9 | 8.9 ± 2.3 | 340 ± 29 | NT | NT | a: 1:Simalikalactone E; 2: Simalikalactone D, 3: Chloroquine; 4: Mefloquine; 5: Primaquine
b: values expressed in nM (or μM when indicated), mean of three independent experiments ± SD
c: not tested
d: lowest concentration tested
e: highest concentration tested

FIGURE 1

Table 2: Inhibition of parasitemia (100% parasitemia is the parasitemia of the mouse treated with DMSO alone) at the 5th day

| Doses | DMSO | CMC | CQ IP[a] (mg/kg/d) | | | SkE IP[b] (mg/kg/d) | | | SkE PO[c] (mg/kg/d) | | |
|---|---|---|---|---|---|---|---|---|---|---|---|
| | | | 1 | 5 | 10 | 0.5 | 1 | 5 | 1 | 10 | 20 |
| Inhibition | 0% | 0% | 0% | 100% | 100% | 59% | 98% | 100% | 55% | 95% | 100% |

FIGURE 2

FIGURE 3

|  | | Survival time | | | |
| --- | --- | --- | --- | --- | --- |
| Treatment | N | Mean [IC$_{95\%}$] | Interpolated mean | p$^1$ | p$^2$ |
| Control | 15 | 4.33 [3.76-4.91] | | | |
| CQ IP 1 | 5 | 7.40 [6.70-8.10] | | 0.013 | |
| CQ IP5 | 5 | 12.80 [11.51-14.09] | | > 0.001 | 0.026 |
| CQ IP 10 | 5 | 19.20 [16.82-21.58]* | 43.87 | > 0.001 | 0.002 |
| SKE IP 0.5 | 5 | 16.40 [11.45-21.35]* | 41.07 | > 0.001 | 0.005 |
| SKE IP 1 | 5 | 18.60 [14.39-22.81]* | 93.89 | > 0.001 | 0.003 |
| SKE IP 5 | 5 | 11.40 [4.51-18.29]* | 20.57 | > 0.001 | 0.047 |
| SKE PO 1 | 5 | 11.00 [6.46-15.54]* | 13.61 | > 0.001 | NS |
| SKE PO 10 | 5 | 12.40 [8.42-16.38]* | 15.01 | > 0.001 | 0.041 |
| SKE PO 20 | 5 | 13.80 [9.32-18.28]* | 16.41 | > 0.001 | 0.014 | p$^1$ = p calculated between the treated group and the control group p$^2$ = p calculated between the treated group and the CQ IP 1 group

* : in the confidence interval, the mean is reduced and
the extreme is not observed (the survival is monitored
only for 21 days).

FIGURE 4

Table 3: Activity and cytotoxicity of SkE on the liver stages of *P. yoelii* malaria and *P. falciparum* malaria

|  | *P. yoelii* | *P. falciparum* |
|---|---|---|
| $IC_{50}$ (µM) | 0.186 ± 0.016 | 1.198 ± 0.187 |
| $TC_{50}$ (µM) | >5.536 | 90.337 ± 9.334 |
| TI | >30 | 75.401 |

FIGURE 5

Figure 6A:
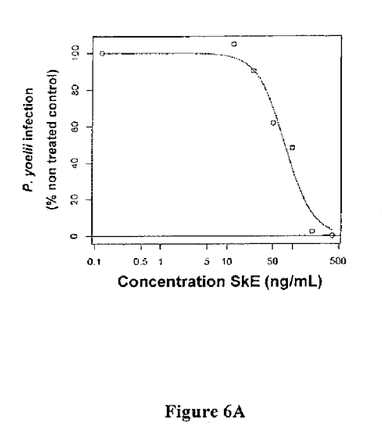
Figure 6B:
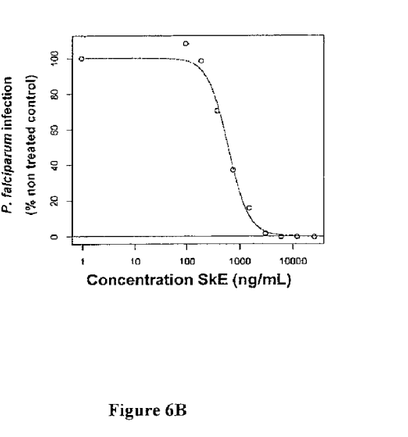

Figure 6A​​​​​​​​​​​​​​​​​​​​​​​​​​​​​​​​​​​​​​​​​​​​​​​​​​​​​​​​​​​​Figure 6B

ISOLATION OF SIMALIKALACTONE E AND USE THEREOF AS A MEDICAMENT, IN THE TREATMENT OF MALARIA

FIELD OF THE INVENTION

The subject of the invention is a novel molecule, Simalikalactone E, which can be extracted from the plant *Quassia amara*, and also the use thereof as a medicament, in particular in the prevention and treatment of malaria.

BACKGROUND OF THE INVENTION

Malaria is one of the three diseases designated by the WHO as being one of the most important in the world, along with HIV/AIDS and tuberculosis. Each year, malaria kills between 1 and 2 million people and affects approximately 500 million, and can lead to a decrease in growth rate ranging up to 1.3% of the GDP in greatly affected countries. A parasite of the *Plasmodium* genus, transmitted to humans via a bite from a female mosquito of the *Anopheles* genus, is responsible for this disease. There are four species responsible for human malaria: *P. vivax, P. malariae, P. ovale* and *P. falciparum. P. vivax* and *P. falciparum* are the most common. Infection with *P. falciparum* is the most severe and can cause death of the patient during a febrile coma. *P. falciparum* malaria is very widespread in sub-Saharan Africa, where an extremely high mortality rate can to a large extent be attributed thereto. Worrying signs attest to the spread of *P. falciparum* malaria to new regions and to its resurgence in areas where it had been eliminated or controlled.

There are only a few molecules active against this disease which are formulated as medicaments, and the emergence of resistance makes the problem of treatment even more acute. It is therefore essential to identify novel molecules which have antimalarial activity.

Among the molecules currently known for their efficacy against malaria, mention may be made of quinine, its derivatives and other compounds: chloroquine, amodiaquine, mefloquine, halofantrine, lumefantrine, and also artemisinin and its derivatives, such as artesunate and arteether or artemether. The most well-known are derived from medicinal plants traditionally used in their country of origin. Quinine is derived from *Cinchona* spp. and artemisinin is derived from *Artemisia annua*.

Some of these molecules can be used either as prophylaxis (prevention when traveling to endemic country) or as therapy (after diagnosis of an infection).

The *Plasmodium* cycle is very complex: in a simplified manner, after a passage in the liver, the parasite rapidly enters the red blood cells of the affected individual, reproduces therein until it causes them to rupture, and invades the neighboring red blood cells. The disease then manifests itself as a fever which is more or less anarchic at the beginning, and then regular after a few multiplication cycles. Some parasites then evolve into gametocytes. These gametocytes make it possible, firstly, for the cycle to continue in the Anopheles mosquito (they are not digested by the mosquito) and, secondly, for genetic mixing to occur since they determine the gametes, which are required for fertilization.

Molecules such as quinine and artemisinin act during the multiplication phase in red blood cells, the erythrocyte phase which is the symptomatic phase. With regard to molecules which have an anti-gametocytocidal activity, the advantage thereof lies in the potential decrease in the rate of transmission of the disease (infectivity) that these molecules could induce, in a group treatment strategy, and also in the possibility of reducing the phenomena of rapid appearance of resistance linked in part to the levels of circulating gametocytes (demonstrated for sulfadoxine-pyrimethamine (SP), and chloroquine (sensitive strains vs resistant strains)). Despite the advantage of using gametocytocidal treatments, there have been few studies aimed at detecting and rationalizing the use of products of this type. Currently, only a few molecules are known to have this property, these being artemisinin and its derivatives, and primaquine. However, primaquine is not the most suitable molecule for use in this way since it has acute toxicity close to its level of activity.

The antimalarial medicaments are not without side effects, and in particular halofantrine has been associated with cardiac problems and mefloquine can exhibit neurological toxicity.

Most of the antimalarial medicaments have a limited lifetime, and lose their efficacy because of the appearance of resistance phenomena. For example, chloroquine, and also the dihydrofolate reductase inhibitors (sulfadoxine/pyrimethamine: Fansidar®) are no longer active on most plasmodium strains and are no longer used in monotherapy. Resistances have also appeared for the artemisinin derivatives, which are the latest medicaments to have been placed on the market. The antimalarials which have become ineffective or are in the process of rapidly losing their effectiveness have been replaced, according to the WHO directives, by ACTs (artemisinin based combination therapies), which combine an artemisinin derivative and another active molecule. However, the effectiveness of this therapeutic strategy combining two molecules is none the less threatened by artemisinin-resistance phenomena.

Furthermore, even though a considerable effort has been made to make these ACTs affordable for the populations in question, their cost still remains high.

We have identified, from a species of the family Simaroubaceae, *Quassia amara* (L.), used in traditional medicine throughout north-west Amazonia and as far as Central America against fevers and malaria, a new molecule, Simalikalactone E (SkE), which has been shown to be active against malaria.

An ethnopharmacological investigation and biological tests had made it possible (Vigneron M. et al., Journal of ethnopharmacology, 2005, 98 (3), 351-360; Bertani S. et al., Journal of ethnopharmacology, 2005, 98(1-2), 45-54) to identify preparations based on mature leaves of *Quassia amara* as advantageous for treating malaria. Antiparasitic tests in vitro and in vivo on mice confirmed the activity of this preparation on malaria (Bertani S. et al., Journal of Ethnopharmacology, 2005, 98(1-2), 45-54). Given the frequency of use of this species in remedies used preventively and curatively against malaria, and the antiparasitic activity detected, a thorough phytochemical study was undertaken in order to identify the components responsible for the activity observed.

A molecule of the quassinoid family with considerable antimalarial activity was isolated from the young leaves of this species: Simalikalactone D (Bertani S. et al., Journal of Ethnopharmacology, 2006, 108(1), 155-157). However, the small amount of Simalikalactone D present in the traditional remedy, prepared from mature leaves of *Quassia amara*, did not make it possible to justify the activity observed in vitro and in vivo for this remedy. Thus, it was sought to identify other active agents responsible for the activity of *Quassia amara* against malaria. Several authors have focused on quassinoids as active ingredients for treating malaria or other pathological conditions: Z. Guo et al., Current Medicinal Chemistry, 2005, 2, 173-190; Guido F et al., International Journal for Parasitology, 1998, 28, 635-640; Curcino Vieira I.

and Braz-Filho R., Studies in Natural Products, Elsevier, 2006, 33, 433-492. However, no molecule has been retained for developing a medicament.

SUMMARY OF THE INVENTION

However, the inventors have succeeded, using mature leaves of *Quassia amara*, in identifying another molecule of the quassinoid family, Simalikalactone E. They have been able to note that this molecule exhibits less toxicity than Simalikalactone D.

Simalikalactone E corresponds to formula 1 below:

1 SkE

It constitutes a first subject of the invention.

This molecule is active in vitro against the strains responsible for malaria and it is active in vivo in a mouse/*Plasmodium vinckei petteri* model, orally. It can therefore be used in the treatment of malaria.

The new quassinoid, Simalikalactone E (SkE), has been isolated from *Quassia amara* (Simaroubaceae), a medicinal plant widely used in Amazonia for treating malaria. This new molecule inhibits 50% of the growth of *P. falciparum* in culture at doses between 24 and 68 nM, independently of the chloroquine sensitivity of the strain tested. It inhibits 50% of the growth of Vero mammalian cells at a dose of 6574 nM, which gives it a selectivity index of greater than 100. We have also shown that this molecule reduces the level of gametocytes by 50% at a concentration 7 times lower than that obtained with primaquine, the reference molecule for this activity. In vivo, on a murine model of malaria, SkE inhibits 50% of the growth of *P. vinckei petteri* at doses of 0.5 and 1 mg/kg/day intraperitoneally and orally, respectively (chloroquine, the reference molecule, inhibits 50% of the growth of *P. vinckei petteri* at a dose of 3 mg/kg/day intraperitoneally).

A second subject of the invention is therefore a medicament comprising SkE and a pharmaceutically acceptable carrier.

In a medicament intended for the treatment and/or prevention of malaria, Simalikalactone E can be used alone or in combination with another antimalarial.

Such a medicament can be administered preventively to individuals who are not suffering from malaria and are temporarily or permanently in areas at risk. It can be administered curatively to individuals suffering from malaria, during an attack but also during the periods of latency of the disease.

A subject of the invention is therefore a medicament comprising SkE, which is indicated for preventing or treating malaria. A subject of the invention is also a medicament comprising SkE, which is indicated for reducing the transmission of malaria.

The suitable administration forms include oral administration forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

The preferred administration routes are the oral, rectal and injectable routes.

A solid composition in the form of tablets can be prepared by mixing the active ingredient, the SkE, with one or more pharmaceutical excipients, such as, for example, gelatin, starch, lactose, magnesium stearate, talc, silica, gum arabic, mannitol, microcrystalline cellulose, hydroxypropylmethylcellulose, or analogous components. The tablets can be coated with sucrose, with a cellulosic derivative or with other materials suitable for coating. The tablets can be prepared by various techniques well known to those skilled in the art, such as direct compression, dry granulation, wet granulation or the hot-melt process.

It is also possible to prepare a composition in the form of gel capsules by mixing the active ingredients with a diluent and pouring the mixture obtained into soft or hard gel capsules.

For parenteral administration, use is made of aqueous suspensions, isotonic saline solutions or sterile injectable solutions which contain pharmacologically compatible dispersing agents and/or wetting agents, for example propylene glycol or butylene glycol.

The daily doses of SkE are advantageously the following: from 0.01 mg/kg/d to 500 mg/kg/d of SkE. In particular, these doses are suitable for oral administration.

There may be particular cases where higher or lower dosages are appropriate; such dosages do not depart from the context of the invention. According to the usual practice, the dosage suitable for each patient is determined by the physician according to the method of administration and the weight and response of said patient to the treatment.

The medicament of the invention is intended to be administered for preferentially 5 to 10 consecutive days, in one or more daily intakes, preferably a single intake per day.

SkE has an equivalent activity in vitro, whether the parasite strains are chloroquine-sensitive or chloroquine-resistant, which makes it possible to envision its use in areas of chloroquine-resistant malaria (Asia, Africa, certain areas of South America, including Guiana).

SkE belongs to a different chemical class compared with all the medicaments currently present on the market for treating malaria. It may therefore be effective on strains resistant to existing medicaments.

The gametocytocidal activity of SkE is seven times greater than that of primaquine, the reference molecule, which also exhibits toxicity problems. It is possible to take advantage of this activity for reducing the transmission rate and the resistance phenomena in the areas where it would be used.

The antimalarial activity of several quassinoids, which are molecules of the same chemical class as SkE, has already been demonstrated. The quassinoids that are active in vivo on mice with malaria are: sergeolide, glaucarubinone, cedronin, bruceolide and its derivatives, and also simalikalactone D (SkD).

The toxicity that we have measured for SkE is less than that of SkD on mammalian cell lines (Vero cells). The selectivity index of SkE with respect to *P. falciparum* is twice that of SkD. SkE therefore provides an advantage over SkD since it is less toxic.

This molecule also acts on the gametocytes, which are the sexual forms of the parasite that infect the Anopheles vector when it draws blood from a contaminated individual. This molecule therefore has an effect on the transmission of the parasite from humans to Anopheles (reduction in the blood gametocyte load, leading to a decrease in infectivity) and also on the possible dissemination of resistances (correlated with the circulating gametocyte level). The latter point could be more particularly taken advantage of in treatments combining several molecules aimed at preventing or delaying these resistance phenomena.

A subject of the invention is also a method for isolating SkE from *Quassia amara* leaves.

SkE can be isolated from dried mature leaves of *Quassia amara* using a protocol which comprises the following steps: the dried mature leaves of *Q. amara* are ground and extracted with methanol. This extract is dissolved in a two-phase system based on n-heptane, ethyl acetate, methanol and water. The lower phase is recovered and its volume is reduced by half by evaporation under reduced pressure. This solution is extracted with ethyl acetate. The ethyl acetate is evaporated off. The residue obtained is dissolved in chloroform and washed with a slightly basic aqueous solution. The organic phase is recovered, dried and concentrated under reduced pressure. This extract is dissolved in ethyl acetate and washed with water. The organic phase is evaporated under reduced pressure and the residue obtained is eluted with ethyl acetate through a silica column.

The extract obtained is purified according to the following protocol: the extract is fractionated by centrifugal partition chromatography using an Arizona H system composed of n-heptane, ethyl acetate, methanol and water, in ascending mode. Samples of 25 ml are recovered. The samples comprising SkE are combined and purified by chromatography on a silica column eluted with cyclohexane/ethyl acetate mixtures of increasing polarity. SkE is eluted with the 50/50 cyclohexane/ethyl acetate mixture.

A subject of the present invention is also a method for treating and/or preventing malaria which comprises the administration, to a patient, of a therapeutically effective dose of SkE. The subject of the invention is also a method for reducing the transmission of malaria, this method comprising the administration, to a population, of therapeutically effective doses of SkE.

BRIEF DESCRIPTION OF THE DRAWINGS

Figures

FIG. 1: table reporting the antiplasmodial activity and the cytotoxicity of SkE.

FIG. 2: table reporting the inhibition of parasitemia.

FIG. 3: survival time of the mice (in days) as a function of the treatment (dose) and of the route of administration (IP/PO). The treatments and the routes of administration are: CQ: chloroquine (1, 5 or 10 mg/kg/day for 4 days); SkE: Simalikalactone E (0.5, 1, 5, 10 or 20 mg/kg/day for 4 days); PO: oral route, IP: intraperitoneal route.

FIG. 4: table reporting the mean survival time of the mice, observed and calculated (interpolated) for the various treatments.

FIG. 5: table reporting the activity and the cytotoxicity of SkE on the liver stages of *P. yoelii* malaria and *P. falciparum* malaria.

FIG. 6: graphic representation of the dose-response effect of SkE on the liver stages of *P. yoelii* infection (A) and *P. falciparum* infection (B) on rodent or human primary hepatocytes.

DETAILED DESCRIPTION OF THE INVENTION

I. Experimental Section

A—Protocol for Obtaining Simalikalactone E:

*Quassia amara* leaves were harvested at Rémire-Montjoly in French Guiana. A specimen (GB3012) was harvested and the botanical identification thereof was confirmed at the Cayenne Herbarium in Guiana.

SkE was isolated from Quassia amara by using the following protocol: 1 kg of dried mature leaves of *Q. amara* are ground and extracted for 24 h with 6 l of methanol, this being carried out twice, to give 200 g of extract. 50 g of this extract are dissolved in 2 l of a two-phase system composed of n-heptane, ethyl acetate, methanol and water in the proportions 3/2/3/2. The heaviest phase is concentrated to 500 ml, and 500 ml of water are added thereto. This solution is extracted with 1 l of ethyl acetate. The ethyl acetate is evaporated off under reduced pressure. The residue obtained is dissolved in 1.5 l of chloroform and washed four times with a 0.001 M solution of sodium hydroxide. The organic phase is recovered, dried over anhydrous magnesium sulfate and concentrated under reduced pressure, to give 3.3 g of extract. This extract is dissolved in 500 ml of ethyl acetate and washed with 500 ml of water. The organic phase is evaporated under reduced pressure and the residue obtained is eluted rapidly with ethyl acetate through a short silica column. After the ethyl acetate has been evaporated off, 1.0 g of extract is obtained. This extract is fractionated by centrifugal partition chromatography (Kromaton apparatus, equipped with a 1 L rotor), using an Arizona H system composed of n-heptane, ethyl acetate, methanol and water in the proportions 1/3/1/3, in ascending mode, at a temperature of 16° C. The flow of solvent is 25 ml/min, and the rotor speed is 1000 rpm and is changed during the elution so as to maintain a pressure of 40 bar. The extract (1.0 g) is dissolved in 40 ml of Arizona H system, filtered and injected. Samples of 25 ml are collected. Samples 14-15-16 are combined to give the fraction F1 (120 mg). This fraction is purified by chromatography on a silica column eluted with cyclohexane/ethyl acetate mixtures of increasing polarity. SkE (10 mg) is eluted with the 50/50 cyclohexane/ethyl acetate mixture. The yield from the plant is 0.004%.

The SkE was characterized by mass spectrometry, by NMR and infrared spectroscopy, and via its optical rotation. Since crystals were obtained from deuterated methanol, an X-ray image of the molecule was also obtained. Its physicochemical characteristics are the following:

Simalikalactone E: APCIMS, 579 ($MH^+$), 561 ($MH^+$—$H_2O$), $^1$H NMR ($CDCl_3$, 500 MHz), δ 6.19 (m, 1H, H-15), 6.17 (s, 1H, H-3), 5.19 (dd, J=2.6, 11.7 Hz, 1H, H-6), 4.75 (d, J=5.1 Hz, 1H, H-11), 4.70 (d, J=2.6 Hz, 1H, H-7), 4.65 (d, J=7.4 Hz, H-17a), 4.19 (s, 1H, H-1), 3.83 (s, 1H, H-12), 3.70 (d, J=7.4 Hz, 1H, H-17b), 3.37 (d, J=11.5 Hz, 1H, H-5), 2.51 (m, 1H, H-24), 2.48 (m, 1H, 1H-19), 2.45 (m, 1H, H-14), 2.43 (m, 1H, H-9), 2.08 (s, 3H, 1H-30), 1.79 (m, 2H, H-21a, H-26a), 1.61 (m, 1H, H-26b). 1.53 (m, 1H, H-21b). 1.45 (s, 3H, H-28), 1.35 (s, 3H, H-29), 1.21 (d, J=7.0 Hz, 3H, H-20), 1.19 (d, J=7.0 Hz, 3H, H-25), 1.01 (t, J=7.4 Hz, 3H, H-22), 0.99 (t, J=7.4 Hz, 3H, H-27). $^{13}$C NMR ($CDCl_3$, 125 MHz), δ 196.5 (C-2), 176.2 (C-23), 1751 (C-18), 166.5 (C-16), 163.0 (C-4), 126.5 (C-3), 82.8 (C-7), 81.8 (C-1), 80.0 (C-13), 79.8 (C-12), 74.2 (C-11), 70.9 (C-17), 69.1 (C-6), 67.3 (C-15), 523 (C-14), 50.4 (C-10), 46.1 (C-8), 45.9 (C-5), 41.3 (C-24), 41.3 (C-19), 41.1 (C-9), 27.2 (C-26), 26.7 (C-21), 26.1 (C-30), 22.8 (C-28), 16.7 (C-20), 15.6 (C-25), 12.5 (C-29), 11.7 (C-22), 11.5 (C-27). IR (KBr, cm$^{-1}$) : 2965, 2926, 2855, 1766, 1738, 1722, 1667. $[\alpha]_D^{26}$=+94° (c=0.35, CHCl$_3$)

B—Biological Activity:

B1—Materials and Methods:

Culturing of *Plasmodium Falciparum*:

The following three strains of *Plasmodium falciparum* were used:

chloroquine-sensitive F32 Tanzania
chloroquine-resistant FcB1 Colombia
W2 Indochina.

The only in vitro culture routinely maintained is the intraerythrocytic stage culture (which corresponds to the clinical manifestations of the disease). All the steps are carried out under a laminar-flow hood (PS2, Jouan) by applying the elementary rules of sterility, so as not to risk any bacterial or fungal contamination of the culture which is performed in the absence of any antibiotic or antifungal molecule (these molecules possibly interfering with the evaluation of the antiplasmodial activities).

The culturing of *P. falciparum* is carried out in sterile culture dishes of 25 or 75 cm$^2$ (supplier: TPP, Switzerland). Each day, the culture medium must be changed and the pH must remain suitable for the survival of the parasite (pH≈7.2-7.4). The techniques used derive from those initially described by W. Trager and J. B. Jensen, Science, 1976, 193(4254): p. 673-675.

The culture medium used is RPMI 1640 (supplier: Lonza, Emerainville). This starting medium is supplemented with 25 mmol/l of Hepes (supplier: Lonza, Emerainville),
200 mM of L-glutamine (supplier: Lonza, Emerainville),
7% v/v of AB human serum (supplier: SHAB, Etablissement Français du Sang [French Blood Bank], Toulouse Rangueil).

Parasitized healthy red blood cells (HRBCs) and also parasitized red blood cells (PRBCs) are then added so as to maintain a hematocrit of approximately 4% and to maintain the parasitemia around 2% (RBC O$^+$, Etablissement Français du Sang [French Blood Bank], Toulouse Rangueil). In order to verify this point, a blood smear is prepared daily from the culture dish and is stained with Diff Quick (supplier: Dade Behring, Paris La Défense). The parasitemia is then evaluated visually by reading under an optical microscope (magnification×100).

If, for example, the parasitemia after reading the smear is 8%, it is necessary to divide the culture pellet by 4 in order to bring said parasitemia back to 2%. The hematocrit is continually maintained at approximately 4%, i.e. 400 µl of red blood cell pellet in approximately 10 ml of medium (25 cm$^2$ dish) or 1.2 ml of red blood cell pellet in approximately 30 ml of medium (75 cm$^2$ dish).

Smear Staining

The Diff Quick® rapid staining set gives results close to those obtained with Giemsa staining and is very quickly used. It is therefore used routinely for evaluating the daily growth of the parasite. The Giemsa technique, which is more laborious, is reserved for the precise parasitemia evaluation (synchronization assays, in vivo evaluation).

Diff Quick®:

The pre-dried blood smears are dipped several times in the Diff Quick® solutions and can thus be fixed and stained in only 30 seconds.

This set comprises 3 reagents

A fixative: Fast Green dissolved in methanol (0.002 g/l)
A 1$^{st}$ dye: eosin dissolved in a phosphate buffer of pH=6.6 (1.22 g/l), and 0.1% (w/v) of sodium azide as preservative.
A 2$^{nd}$ dye: thiazine dye dissolved in a phosphate buffer of pH=6.6 (1.1 g/l).

Technique for Use:

The various reactants first will be placed in staining dishes with lids, or any other appropriate container.

The smears are then dipped in and out of the fixative 5 times in a row for one second, and then in and out of the 1$^{st}$ dye 7 times in a row for one second, and finally in and out of the 2$^{nd}$ dye 20 times in a row for one second.

A single immersion for 5, 7 or 20 seconds gives poor staining.

The excess solution must be rapidly drained off between each reagent.

After drying, the slides can be read under an optical microscope.

Giemsa:

Giemsa is a neutral stain composed of an acid dye: azure eosinate, and of basic dyes: methyl violet, methyl blue and methyl azure, which precipitates in water. The precipitate obtained is insoluble in water but soluble in methyl alcohol.

The acidic cell components are selectively stained with the basic dyes. These components are described as basophilic (parasitic DNA) and are stained blue-violet.

The basic cell components are selectively stained with the acid dyes. These components are described as acidophilic or eosinophilic (red blood cell cytoplasm) and are stained orangey-pink.

The neutrophilic components are stained both with the acid dyes and the basic dyes.

Preparation of a Giemsa Stock Solution:

1.52 g of Giemsa (supplier: Sigma, G5637-25G) are added, in an Erlenmeyer flask covered with aluminum foil (protection against light), to 100 ml of glycerol (supplier: Sigma Ultra, G6279-1L) heated for a few minutes in a water bath at 60° C.

The mixture is then stirred magnetically for approximately 4 hours at ambient temperature. Methanol (100 ml) is added and the container is left to stir magnetically overnight.

The following day, the stirring is stopped. The preparation is left to stand for one week, and is then filtered using pleated filter paper No. 3 in a flask protected against light.

Preparation of a Stock Solution of Buffer of pH=7.2:

2 g of potassium phosphate (KH$_2$PO$_4$) and 5 g of sodium phosphate (Na HPO$_4$.H$_2$O) are added to 1 L of distilled water.

Extemporaneous Preparation of Smear Staining Solution:

This solution is obtained by diluting the Giemsa stock solution to 10% in the buffer solution. The smears are then dipped into the solution using a slide holder, and rinsed with water after approximately 20 min of contact. After drying, the slides can be read under an optical microscope.

Synchronization of the Culture by Lysis of the Old Forms In Vitro:

This technique (Lambros, C. and J. P. Vanderberg, The Journal of Parasitology, 1979, 65(3): p. 418-420) is generally carried out on a culture before performing anti-plasmodial activity evaluation tests in vitro, in order to reconstitute the conditions of synchronous development of the parasite that are observed in vivo. It makes it possible to eliminate the old parasitic forms and to keep only a single stage, the young forms in the ring stage. This technique also makes it possible, in combination with a selective enrichment in old form (Ribaut, C., et al., Malaria Journal, 2008, 7(1): p. 45), to evaluate the parasitic stage on which the molecule tested preferentially acts.

Principle:

During its intraerythrocytic multiplication, the parasite needs a large amount of nutrients for its metabolism. Since the host cell has limited resources, the parasite will permeabilize the erythrocyte membrane so as to increase transmembrane trafficking of substrates and catabolites. Red blood cell permeability increases with the aging of the parasites. The high hexitol permeability of erythrocytes infected with *P. falciparum* is therefore used to selectively lyze the red blood cells infected with old parasites (schizont stage). Only the young parasitic forms, ring stages, survive.

Technique:

5 g of D-sorbitol (Sigma, France) are solubilized in 100 ml of distilled water. The whole mixture is then filtered by passing it through a 0.22 μm millipore filter (Millex GV, Cork) in order to obtain a sterile solution. The culture to be synchronized must have a predominance of young (ring) forms. After centrifugation of said culture for 10 minutes, at 450 g, the supernatant is removed.

The sorbitol solution previously prepared and heated to 37° C. is added dropwise to the culture pellet. After homogenization, the whole is kept in a water bath at 37° C. for 10 minutes.

A further centrifugation is then carried out, the supernatant containing the sorbitol is removed and two washes of the red blood cell pellet are carried out with serum-free RPMI. The red blood cell pellet is then put back in culture in a dish containing complete medium prepared beforehand and kept at 37° C.

Evaluation of Antiplasmodial Activity:

The antimalarial activity of the various products is evaluated by means of the radioactive method using tritiated hypoxanthine, described by Desjardins et al., with the modifications introduced by Benoit et al. (Desjardins R. E. et al., Antimicrob. Agents Chemother, 1979, 16: 710-718; F. Benoit et al. Trans. Roy. Soc. Trop. Med. Hyg. 89: 217-218).

The test is carried out in 96-well culture plates (supplier: TPP, Switzerland) on cultures mainly at the ring stage. The parasites are brought into contact with the products for 48 h at 37° C. and 5% $CO_2$. The growth of the parasite is then estimated by following tritiated hypoxanthine incorporation into the nucleic acids of the parasite. The $IC_{50}$ values are determined graphically on curves of percentage inhibition of growth as a function of concentration. Thus, the antimalarial activity of SkE was evaluated according to the following protocol.

For each test substance, the wells are seeded with 100 μl of solution containing the parasitized red blood cells (solution with 1.5% parasitemia, 2% hematocrit) and then 100 μl of increasing dilution of SkE (stock solution prepared in DMSO, dilution in the complete culture medium) are added thereto.

Once prepared, the plates are placed in an incubator for 24 h (37° C., 5% $CO_2$ and humid atmosphere). Chloroquine, the control molecule, is directly solubilized in RPMI at 37° C., supplemented with 10% serum.

After incubation for 24 h, 20 μl of a solution of tritiated hypoxanthine diluted to 0.37 GBq/ml in RPMI are added to each well (tritiated hypoxanthine 1 mCi/ml, Perkin Elmer). The plates are then incubated for 24 h, and then frozen in order to cause lysis of the red blood cells.

The plates are thawed for approximately one hour at ambient temperature. The red blood cells are then collected on a filter (Printed Filtermat A filter, 1450-421, Wallac Perkin Elmer) by means of a cell harvester (Filtermate Harvester, Packard). The filter is then dried at ambient temperature. Once dry, it is placed in a bag (Sample Bag, 1450-432, Perkin Elmer) which is sealed, and then 2 ml of scintillation fluid (Perkin Elmer) are added.

The filter is then placed in a cassette which is placed in the β-counter in order to measure the radioactivity. The results are expressed on curves giving the inhibition of incorporation relative to a control which does not receive any active ingredient (0% inhibition) as a function of the concentration of active ingredient tested. An $IC_{50}$ (concentration which inhibits 50% of parasite growth) is then calculated graphically.

Evaluation of Cytotoxicity:

This evaluation is carried out on two cell types, the MCF-7 line, which is a mammary tumor cell line, and Vero cells (monkey kidney cells).

The MCF-7 cells are cultured in DMEM medium enriched with 10% fetal calf serum (FCS). Twice a week, when the cells are confluent, it is necessary to subculture (passage) them, i.e. to detach them from their support in order to take them up again so as to perform other cultures or tests. The passaging is carried out by adding 3 ml of trypsin-EDTA (Sigma) to the cell monolayer and then leaving to incubate for 3 minutes at 37° C. The trypsin-EDTA, by digesting the extracellular matrix, makes it possible to detach the adherent cells and then to recover them in suspension. The reaction is stopped by adding DMEM with FCS. The number of cells is then evaluated on a Malassez cell. Vital staining with Trypan blue is carried out in order to determine the percentage of dead cells (which should not exceed 30%).

The cells are re-seeded at 3 million per 75 $cm^2$ dish in 30 ml of DMEM+10% FCS, and placed in the incubator (37° C., humidified air, 5% $CO_2$).

VERO cells are monkey kidney epithelial cells. They are cultured in the same way as the MCF-7, but in EMEM medium supplemented with 10% FCS, nonessential amino acids, sodium pyruvate, HEPES and glutamine.

The evaluation of cytotoxicity follows the same method as the antimalarial activity test, but with *P. falciparum* being replaced with the MCF-7 or VERO cells.

However, there are a few minor modifications, owing to the different mode of culture. This is because the cells used for the cytotoxicity tests are adherent cells and their growth is slower. Consequently, they are seeded in 96-well plates 24 hours before they are brought into contact with the test products. After 24 h, the cells adhere to the bottom of the well, the medium is changed, and then the test molecules are added, the dilution thereof being carried out in complete medium. The medium used depends on the cells used (DMEM or EMEM).

In the same way as for the antimalarial activity test, tritiated hypoxanthine is added 24 hours after bringing into contact with the products, and the plate is placed in the freezer 48 hours later. Finally, the radioactivity is measured as for the antimalarial activity test. The evaluation of the $IC_{50}$ values is carried out graphically as for that of *P. falciparum*.

Evaluation of Gametocytocidal Activity

The gametocytocidal activity is evaluated only on the W2 strain culture. The technique used derives from that described by Ifediba and Vanderberg (Ifediba, T. and J. P. Vanderberg, Nature, 1981, 294 (5839): p. 364-366) with the modifications described by Sall et al. (Sall, C., et al., Bioorganic & Medicinal Chemistry Letters, 2008. 18(16): p. 4666-4669). The culture, after lysis with D-Sorbitol, is adjusted to a parasitemia of 2% (hematocrit 4%). The culture dishes (75 $cm^2$) are kept vertical with a complete medium containing, in addition, 200 mM of hypoxanthine. This medium is changed daily for 11 days. At this time, N-acetylglucosamine is added to the medium. Two days later, the gametocytes are distributed into a 24-well plate and the active ingredients are added at increasing concentration (triplicates). Forty-eight hours later, smears are performed on each well. The gametocytemia is evaluated visually and a curve giving the percentage inhibition relative to the control (well without active ingredient) as a function of concentration is plotted. The $IC_{50}g$ (gametocyte) is then determined graphically. The control used is primaquine, a reference gametocytocidal antimalarial.

Evaluation of Antimalarial Activity In Vivo

The antimalarial activity of SkE was evaluated on female Swiss mice (22 g±2) infected with *P. vinckei petteri*. Before infection of the mice having been used for the test, the parasites were thawed, injected and maintained by passaging in two batches of mice. The parasitized blood was taken from the retro-orbital sinus and each mouse of the study was infected with $2 \times 10^7$ parasites intraperitoneally. The infected animals were divided up into batches of 5 per cage and were treated intraperitoneally each day for 4 days. The SkE was tested at 4 concentrations prepared in 90% DMSO (intraperitoneal route) or carboxymethylcellulose (oral route) in such a way that each mouse receives 200 µl of preparation. The experiment included control parasitized mice receiving 200 µl of 90% DMSO or CMC alone orally, and 3 batches of 5 mice, each of these batches being treated with solutions of chloroquine at 1, 5 and 10 mg/kg diluted in PBS (IP).

At the end of the treatment (5 d after the infection), a blood smear was performed from a drop of blood originating from the tail of each mouse, fixed with methanol and stained with Giemsa. The slides were examined under a microscope and the parasitemia counted for 10 000 red blood cells.

The survival of the mice was monitored for 21 days.

Evaluation of the In Vitro Activity of Simalikalactone E (SkE) Against the Liver Stages of *Plasmodium yoelii* and *Plasmodium falciparum*:

The in vitro activity of SkE against the pre-erythrocytic stages was tested on different *Plasmodium* species. The sporozoites were obtained from infected salivary glands of *Anopheles stephensi* mosquitoes fed with a continuous culture of *P. falciparum* (coll. R. Sauerwein, The Netherlands) or of mice parasitized with *P. yoelii* (Insectarium of INSERM Unit 945). The in vitro assays were carried out using cultures of human primary hepatocytes (HH) or mouse primary hepatocytes (MH), respectively. The primary cells were isolated by collagenase perfusion of pieces of liver (obtained from humans or from female Swiss mice, respectively), followed by purification of the separated cells on a percoll gradient. The hepatocytes were seeded into 96-well microplates (35 000 MH/well and 82 500 HH/well) and maintained in culture at 37° C. and 5% $CO_2$ in a William medium supplemented with 10% FCS (Hyclone), 100 U/ml of penicillin, 100 mg/ml of streptomycin, 2 mM of glutamine, 5 µg/ml of insulin and $5 \times 10^{-7}$ M of hydrocortisone hemisuccinate. A stock solution of SkE was prepared in DMSO at 200 mg/ml, and then diluted in complete medium described above so as to obtain the desired concentrations. The hepatocytes were infected with *P. yoelii* sporozoites (30 000) or *P. falciparum* sporozoites (40 000). The SkE compound was added simultaneously with sporozoites at various concentrations. The culture medium was then replaced 3 h after the inoculation of the sporozoites, and then every day. The cultures were fixed 48 hours after the infection for *P. yoelii*, and 5 days after infection for *P. falciparum*. The inhibitory effect of the compound was quantified, after fluorescent immunolabeling of the liver schizonts with a mouse serum directed against PfHSP70, by fluorescence microscopy analysis. The activity was evaluated with the Excel software for calculating the IC50, the concentration which inhibits 50% of the infection relative to the untreated control.

Evaluation of the In Vitro Cytotoxicity of SkE on Primary Rodent Hepatocytes or on Primary Human Hepatocytes In parallel, the cytotoxicity of the compound was evaluated on human and rodent hepatocytes treated under the same conditions as in the assays for activity of the test compound, by means of the MTT (tetrazolium) colorimetric assay (Mosmann et al., 1983). After incubation of the primary rodent or human hepatocytes for 2 days or 5 days, respectively, with the various concentrations of the test compound, 100 µl of MTT solution (500 µl/ml) were added to each well. The plates were then incubated for 4 hours at 37° C. The formazan crystals were then dissolved in 100 µl of DMSO-ethanol mixture (V/V). The optical density was measured by spectrophotometry at 540 nm. The results are expressed as percentage cell viability relative to the untreated control.

Figure 1:
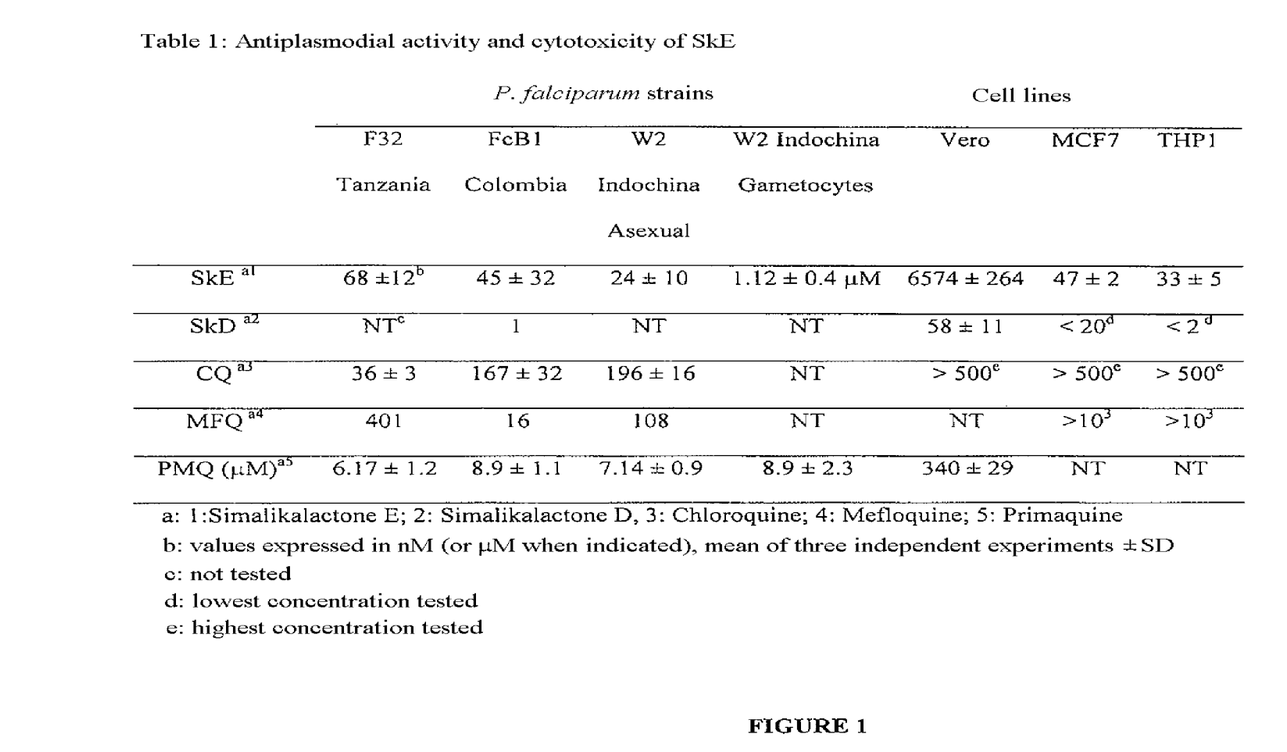

B2-Results:

The antiplasmodial activity of SkE was determined in vitro and in vivo. The results are reported in the table of FIG. 1.

In vitro, on three different strains of *P. falciparum*, SkE has IC50 values of between 24 and 68 nM. The activity does not depend on the level of chloroquine resistance of the strain used.

Figure 2:
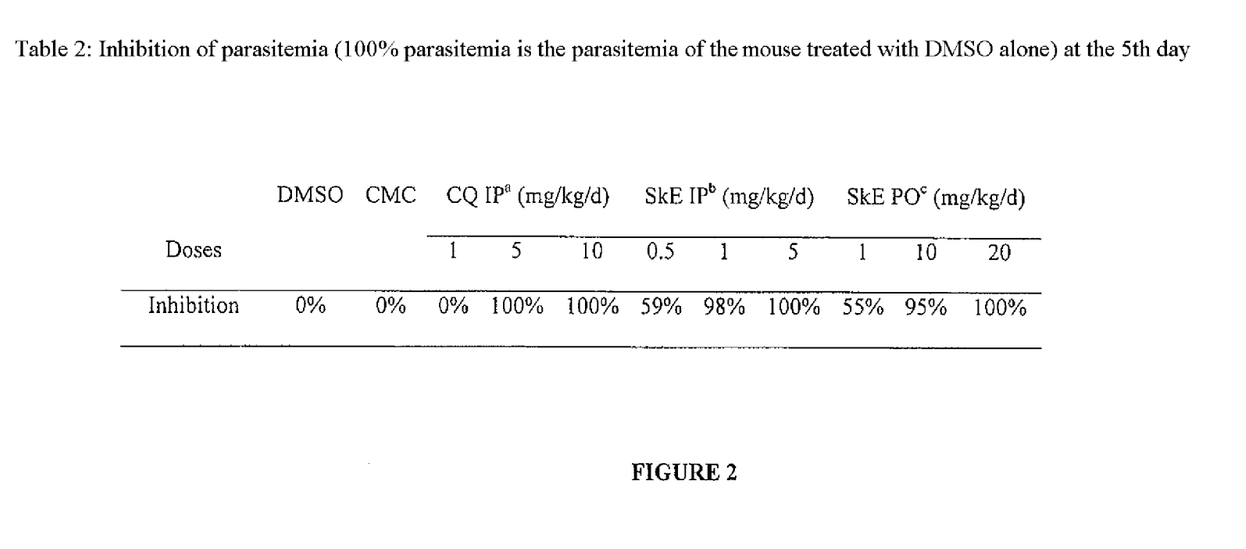

In vivo, SkE is active orally (PO) or intraperitoneally (IP) on mice infected with *P. vinckei petteri*, according to the Peters test protocol. The IP route (effective dose 50, corresponding to the dose which confers a parasitemia on average equal to 50% of that of the controls: $ED_{50}$=0.5 mg/kg/day) is more effective than the PO route ($ED_{50}$=1 mg/kg/day), the control being chloroquine ip ($ED_{50}$=3 mg/kg/day) (table of FIG. 2).

Figure 3:
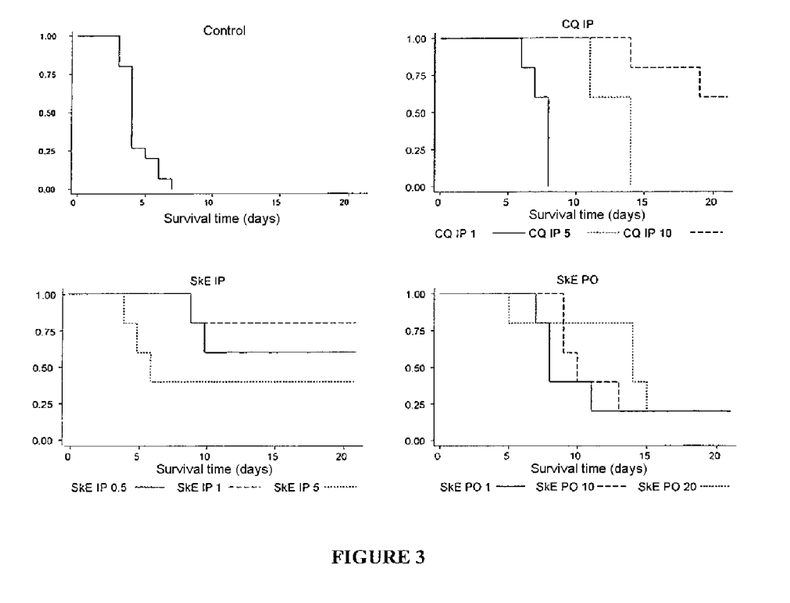
Figure 4:
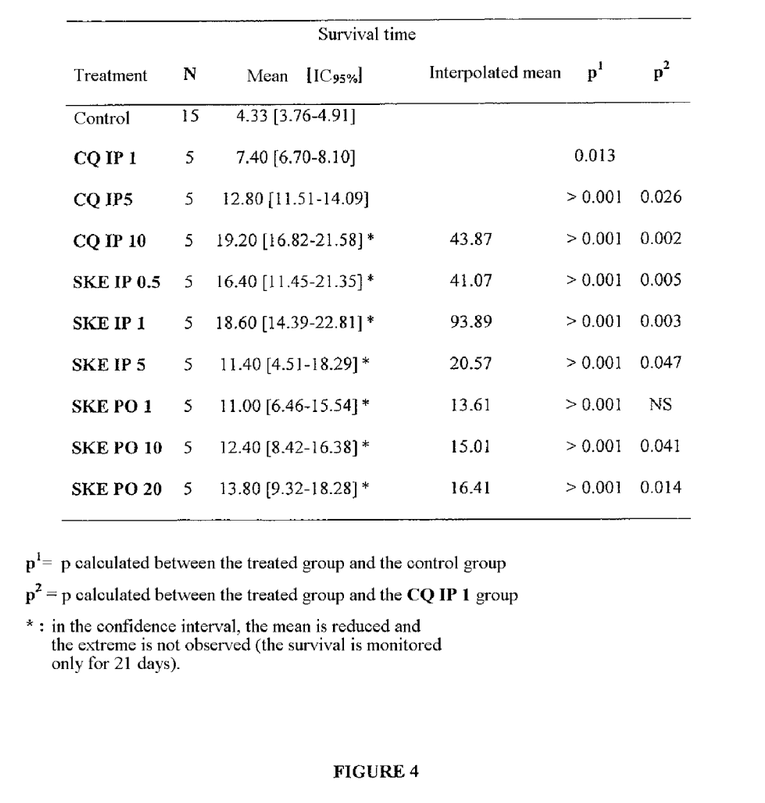

The survival of the mice was monitored for 3 weeks and the survival time is given for one experiment (FIG. 3 and table 3). The mean survival time of the mice treated with SkE ip at 1 mg/kg/day is greater than 18.6 days, and similar to that of the mice treated with chloroquine ip at 10 mg/kg/day.

The appearance of the survival curves (FIG. 3) reveals that, for the IP route, the dose of 1 mg/kg/d is equivalent to what is obtained for CQ at 10 mg/kg/d; furthermore, via the IP route, the survival of the mice is always better than that of the mice treated with CQ at the doses of 1 confirmed by table 1 where p<0.05 (hypothesis of a 95% probable statistically significant difference). A same significant difference is found when the SkE IP 0.5 and 1 groups are compared with CQ at 5 mg/kg/d (p<0.05).

The following cytotoxic activities were also demonstrated:

The cytotoxicity of SkE depends on the cells used for its evaluation and ranges from 6 µM (Vero cells) to 33 nM (THP1 cells).

SkE also acts on the sexual forms of the parasite (gametocytes), and has an excellent gametocytocidal activity, seven times greater than primaquine, which is the reference molecule.

The activity of SkE on murine hepatocytes infected with *P. yoelii*. A mean calculated on three experiments gave an IC50 of 186±16 nM (see table of FIG. 5 and FIG. 6A). If compared with primaquine, the medicament of reference, under the same conditions, SkE is at least 3 times more active than primaquine (IC50=640 nM). In parallel, the cytotoxicity was evaluated: toxicity was observed in one of the 3 experiments carried out (IC50=1.12 µM), whereas in the other two, no toxicity was observed with the highest concentration tested (5.54 µM).

Figure 5:
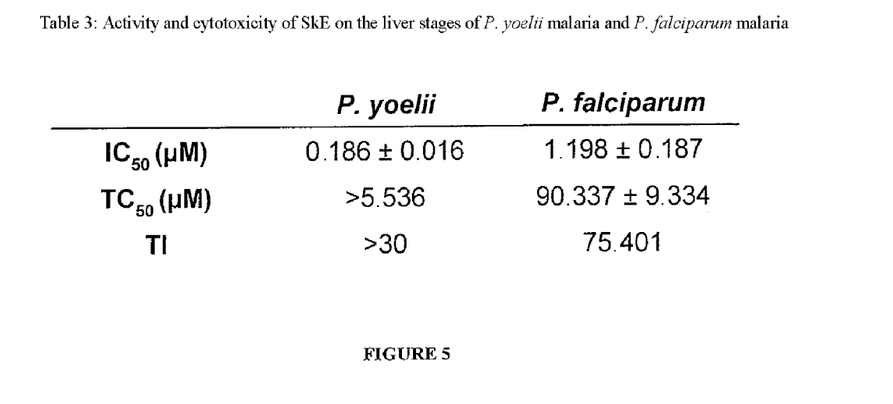

SkE is also active against the liver stages of *P. falciparum* (IC50=1.198±0.19 µM, mean calculated on two experiments) (table of FIG. 5 and FIG. 6B).

The activity observed is less than that observed on the rodent plasmodia, but close to that observed with primaquine ($IC_{50}$=0.80 μM) on the same species. In addition, the therapeutic index, calculated by the formula $TI=TC_{50}/IC_{50}$ (TI=75), is comparable to that of primaquine (TI=81).

The invention claimed is:

1. A molecule corresponding to formula 1 below:

1 SkE

2. A medicament comprising the molecule of formula 1 as claimed in claim 1, and a pharmaceutically acceptable carrier.

3. The medicament as claimed in claim 2, for reducing the transmission of malaria.

4. The medicament as claimed in claim 2, which is intended for oral administration, rectal administration, administration by injection, or topical administration.

5. The medicament as claimed in claim 2, in which the daily dose of the molecule of formula 1 is from 0.01 mg/kg/d to 500 mg/kg/d.

6. A method for isolating the molecule of formula 1 as in claim 1 for isolating the molecule from dried mature leaves of *Quassia amara* which comprises the following steps: the dried mature leaves of *Q. amara* are ground and extracted with methanol, this extract is dissolved in a two-phase system based on n-heptane, ethyl acetate, methanol and water, the lower phase is recovered and its volume is reduced by half by evaporation under reduced pressure, this solution is extracted with ethyl acetate, the ethyl acetate is evaporated off, the residue obtained is dissolved in chloroform and washed with a slightly basic aqueous solution, the organic phase is recovered, dried and concentrated under reduced pressure, this extract is dissolved in ethyl acetate and washed with water, the organic phase is evaporated under reduced pressure and the residue obtained is eluted with ethyl acetate through a silica column.

7. A method for treating malaria comprising administering a molecule corresponding to formula 1 below:

1 SkE

8. The method of claim 7, wherein the molecule is administered via oral administration, rectal administration, administration by injection, or topical administration.

9. The method of claim 7, wherein a daily dose of the molecule of formula 1 is from 0.01 mg/kg/d to 500 mg/kg/d.

* * * * *

UNITED STATES PATENT AND TRADEMARK OFFICE
CERTIFICATE OF CORRECTION

PATENT NO. : 8,604,220 B2
APPLICATION NO. : 13/378888
DATED : December 10, 2013
INVENTOR(S) : Jullian et al.

It is certified that error appears in the above-identified patent and that said Letters Patent is hereby corrected as shown below:

Title Page,
Item (73) Assignee: "Institut de Recherche Pour le Development, Marseille Cedex (FR)"
should read --Institut de Recherche Pour le Developpement, Marseille (FR)--.

In the claims:
Column 13,
Line 35, "claim 1 for isolating the molecule from dried mature leaves of" should read
--claim 1 from dried mature leaves of--.

Signed and Sealed this
Twenty-ninth Day of April, 2014

Michelle K. Lee
*Deputy Director of the United States Patent and Trademark Office*